US00PP30762P3

(12) United States Plant Patent
Wood

(10) Patent No.: US PP30,762 P3
(45) Date of Patent: Jul. 30, 2019

(54) ***THUJA* PLANT NAMED 'SMNTPGF'**

(50) Latin Name: *Thuja plicata*
Varietal Denomination: SMNTPGF

(71) Applicant: Timothy Wood, Spring Lake, MI (US)

(72) Inventor: Timothy Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 15/732,609

(22) Filed: Nov. 30, 2017

(65) Prior Publication Data

US 2019/0166743 P1 May 30, 2019

(51) Int. Cl.
*A01H 7/00* (2006.01)

(52) U.S. Cl.
USPC ..... Plt./213

(58) Field of Classification Search
USPC ..... Plt./213
CPC ... A01H 7/00; A01H 5/00; A01H 5/02; A01H 5/04; A01H 5/025
See application file for complete search history.

(56) References Cited

PUBLICATIONS

Spring Meadow Nursery Floweriung Shrubs Starter Plants Catalog and Shrub Reference 2017-2018, retrieved on Nov. 1, 2018, retrieved from the Internet at https://springmeadownursery.com/files/resource_files/2017-18_SMN_Catalog_1-50.pdf, pp. 1-9, 24 and 88 (Year: 2017).*

* cited by examiner

*Primary Examiner* — June Hwu
(74) *Attorney, Agent, or Firm* — Cassandra Bright

(57) ABSTRACT

A new and distinct *Thuja* cultivar named 'SMNTPGF' is disclosed, characterized by bright green and yellow foliage, with this bright coloration maintained in cold temperatures. Cold hardiness of the new variety is observed to USDA Zone 5. Deer resistance has been observed as well. Plants are pyramidal, dwarf and rapid growing. The new cultivar is a *Thuja*, suitable for ornamental garden purposes.

2 Drawing Sheets

Latin name of the genus and species: *Thuja plicata.*
Variety denomination: 'SMNTPGF'.

BACKGROUND OF THE INVENTION

The new cultivar, hereinafter referred to as 'SMNTPGF', was discovered by the inventor, Timothy Wood, in a commercial nursery in Grand Haven, Mich. This new discovery is the result of an open-pollination of the seed parent *Thuja plicata* '4EVER', U.S. Plant Pat. No. 19,267 with unidentified pollen parents during 2006.

After identifying the new variety as a potentially interesting selection during 2011, the inventor first organized propagation of 'SMNTPGF' by softwood cuttings at the same commercial nursery during 2011. The inventor continued controlled testing and propagation, assessing stability of the unique characteristics of this variety. At least five generations have been reproduced and have shown that the unique features of this cultivar are stable and reproduced true to type.

SUMMARY OF THE INVENTION

The cultivar 'SMNTPGF' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SMNTPGF' These characteristics in combination distinguish 'SMNTPGF' as a new and distinct *Thuja* cultivar:

1. Fast growing dwarf plant.
2. Deer resistance.
3. Bright foliage coloration during cold conditions.
4. Hardy to Zone 5.

COMPARISON TO PARENT VARIETY

'SMNTPGF' is similar in most horticultural characteristics to the parent variety *Thuja plicata* '4EVER'. Plants of the new cultivar 'SMNTPGF' however, differ in the following:

1. New cultivar has lime and gold coloration; parent has lime green coloration.
2. New cultivar has fuller branches; parent is not as full.

COMMERCIAL COMPARISON

*Thuja* 'SMNTPGF' can be compared to the commercial variety *Thuja plicata* 'Daniellow', U.S. Plant Pat. No. 20,267. Plants are similar in most horticultural characteristics, however, plants of the new variety differ in the following:

1. 'SMNTPGF' has lime and gold coloration; comparator has golden yellow and orange coloration.
2. 'SMNTPGF' is a fuller plant; comparator is more conical.

3. 'SMNTPGF' is a dwarf plant; comparator is a medium sized plant.

BRIEF DESCRIPTION OF THE PHOTOGRAPHS

Figure 1:
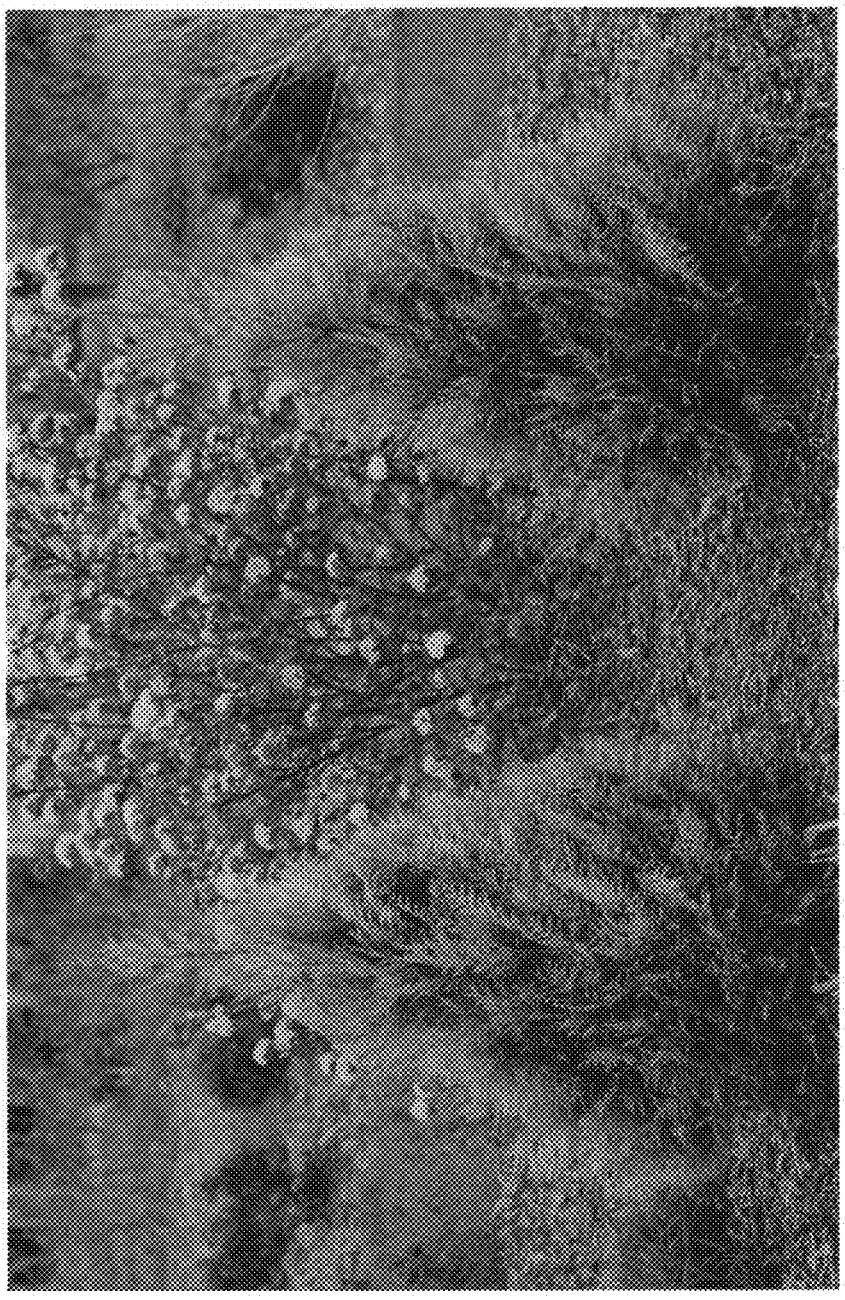

The accompanying photograph in FIG. 1 illustrates in full color a typical plant of 'SMNTPGF' grown outdoors in Grand Haven, Mich. The plant is approximately 2 years old, and is shown growing in the ground.

Figure 2:
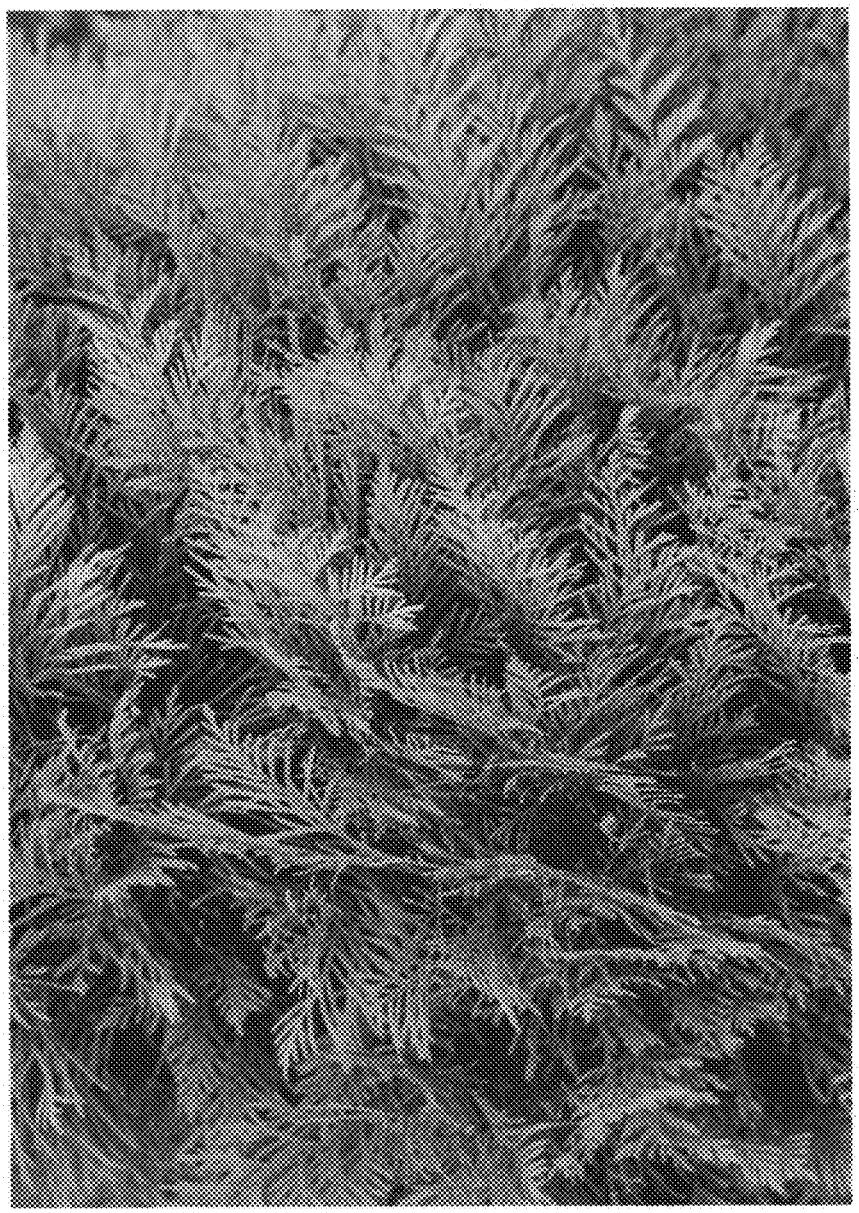

FIG. 2 shows a close up of typical foliage of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used, The following observations and measurements describe 'SMNTPGF' plants grown outdoors in Grand Haven Mich. Plants are approximately 2-3 years old, in a 3 gallon nursery container. Measurements and numerical values represent averages of typical plant types.

Botanical classification: *Thuja plicata* 'SMNTPGF'.

PROPAGATION

Time to rooting: 60 to 90 days at approximately 40-50° F.

Root description: Thick to fine, fibrous and fleshy, moderate branching. Colored white to tan, not accurately measured with the R.H.S. chart.

PLANT

Growth habit: Upright, pyramidal.

Height: 129 cm.

Plant spread: 60 cm.

Typical growth rate: Rapid. Branchlets growing on average 15 to 25 cm in a season, depending upon maturity and environmental conditions.

Pinching required: Some pinching encourages better branching.

Branching habit: Outwards from center stem.

Length of lateral branches: 37 cm.

Average number of lateral branches: 25-50.

Diameter of lateral branches: 1 cm.

Lateral branch color: Brown N200B.

Lateral branch strength: Strong.

*Branchlet orientation*.—Vertical, upright fan spray.

Internode length: 1.25 cm, on average.

Trunk bark:

*Color*.—Near RHS Brown 200C with scales Greyed-Orange 175C.

*Texture*.—Rough, moderately scaly.

FOLIAGE

Leaf:

*Arrangement*.—Alternate, scales.

*Shape*.—Scale-like.

*Average length*.—5 mm.

*Average width*.—1 mm.

*Apex*.—Acuminate.

*Base*.—Truncate.

*Margin*.—Entire.

*Texture of top surface*.—Smooth, like plastic.

*Texture of bottom surface*.—Smooth, like plastic.

*Color*.—Young foliage upper side: Yellow 6A, fades into mature color. Young foliage under side: Yellow Green N144B. Mature foliage upper side: Yellow Green N144B. Mature foliage under side: Mix of Yellow 6A and Green 143B. Mature foliage in winter upper side: Yellow Green N144B. Mature foliage in winder under side: Mix of Yellow 6A and Green 143B.

*Venation*.—Indistinguishable from leaf blade.

*Fragrance*.—None.

FLOWER

Flowering not observed.

OTHER CHARACTERISTICS

Disease and pest resistance: Deer resistant. No other resistance nor susceptibility observed.

Drought tolerance: No tolerance for drought.

Temperature tolerance: −29° C. to 39° C.

What is claimed is:

1. A new and distinct cultivar of *Thuja* plant named 'SMNTPGF' as herein illustrated and described.

* * * * *